United States Patent [19]

Nakamura et al.

[11] 4,145,272
[45] Mar. 20, 1979

[54] OXYGEN SENSOR

[75] Inventors: Koyo Nakamura, Yokosuka; Masayasu Nakajima, Yokohama; Akihiro Ohnishi, Koshigaya, all of Japan

[73] Assignee: Nissan Motor Company, Limited, Japan

[21] Appl. No.: 826,547

[22] Filed: Aug. 22, 1977

[30] Foreign Application Priority Data

Aug. 23, 1976 [JP] Japan .................. 51-112761[U]

[51] Int. Cl.² .............................. G01N 27/46
[52] U.S. Cl. ................... 204/195 S; 60/276; 123/119 E; 123/119 EC
[58] Field of Search ............... 204/195 S, 1 S; 60/276; 123/119 E, 119 EC; 324/29, 71 R

[56] References Cited

U.S. PATENT DOCUMENTS

| | | | |
|---|---|---|---|
| 3,844,920 | 10/1974 | Burgett et al. | 204/195 S |
| 3,891,529 | 6/1975 | Beesch | 204/195 S |
| 3,941,673 | 3/1976 | Takao et al. | 204/195 S |
| 3,960,692 | 6/1976 | Weyl et al. | 204/195 S |
| 3,960,693 | 6/1976 | Weyl et al. | 204/195 S |
| 3,981,785 | 9/1976 | Sandler | 204/195 S |
| 4,029,472 | 6/1977 | Micheli et al. | 60/276 X |
| 4,076,608 | 2/1978 | Fujishiro et al. | 204/195 S |

Primary Examiner—G. L. Kaplan
Attorney, Agent, or Firm—Lowe, King, Price & Becker

[57] ABSTRACT

A platinum reference electrode is disposed on the surface of a blind bore formed in a body of solid zirconia electrolyte and two semi cylindrically shaped measuring electrodes one platinum the other gold are disposed on the outer surface of the body. A first annular insulator supports the body within the casing and defines two chambers on either side thereof while a second annular insulator supports and presses lead wires against the measuring electrodes. A cylindrical connector is inserted into the blind bore to provide good electrical connection between the platinum reference electrode and a lead line.

Atmospheric air enters the first chamber and the blind bore while exhaust gases enter the second chamber and contact the measuring electrodes; the platinum/platinum and platinum/gold electrodes produce markedly different signals one of which is used to recalibrate the other as the peak output voltages decrease with time and temperature.

2 Claims, 5 Drawing Figures

OXYGEN SENSOR

BACKGROUND OF THE INVENTION

1. Field of the Invention

This invention relates to a gas sensor and more particularly to an oxygen sensor suitable for use in a closed loop control unit which controls the air-fuel ratio of the air fuel mixture fed to an internal combustion engine.

2. Description of the Prior Art

As is well known, oxygen sensors usually comprise a solid electrolyte and two metallic electrodes formed thereon, one of which is exposed to a reference gas and the other of which is exposed to a gas the oxygen concentration of which is to be measured. The solid electrolyte, which, by way of example, is typified by Zirconia ($ZrO_2$), when combined with the two electrodes acts as a source of electromotive force (EMF) on exposure to gases having different oxygen concentration. This phenomenon is brought about by a difference in the oxygen partial pressure exerted on the surface on each electrode. The greater the partial pressure difference becomes, the greater the voltage developed by the sensor becomes. However, the partial pressure existing on the surface of the measuring electrode, as it will be referred to hereinlater, is greatly influenced by the metal constituting same. To develop a greater understanding of this effect of the metal on the partial pressure of the oxygen exerted on the measuring electrode, it is considered advantageous at this time to consider the content of the exhaust gases and the chemistry of the reaction, if any which takes place of the afore mentioned measuring electrode.

Theoretically if an exactly stoichiometrical air fuel mixture i.e. a mixture having an exactly stoichiometrical air fuel ration, is combusted in a combustion chamber of an internal combustion engine, then the exhaust gases should contain no oxygen viz. all of the oxygen should be consumed in the combustion. However perfect combustion cannot be realized practically, thus there is always some oxygen, carbon monoxide and hydrocarbon (uncombusted fuel) contained in the exhaust gases emitted from an internal combustion engine. This is true even if a richer than stoichiometric mixture is combusted, that is to say there is insufficient oxygen for complete combustion of the hydrocarbon fuel contained in the air-fuel charge fed into the combustion chamber or chambers. In the case of a leaner than stoichiometrical mixture, there is of course always an excess of oxygen.

Now if the metal employed as the measuring electrode of an oxygen sensor possess catalytic oxidizing properties, i.e. induces oxidation on the surface thereof, and the electrode is exposed to the flow of exhaust gases resulting from the combustion of a mixture having an air fuel ratio greater than the stoichiometric ratio (i.e. is leaner than a stoichiometric mixture), an oxidation reaction will occur on the surface thereof wherein the carbon monoxide and hydrocarbon material will be oxidized to carbon dioxide and water.

However since there is an excess of oxygen remaining after the oxidation reaction, there will still be some oxygen present on the surface to create a partial pressure thereon. The partial pressure difference between the reference electrode and the measuring electrode is thus reduced and the voltage produced by the sensor under these conditions is relatively small. This effect is shown graphically in FIG. 4A on the right hand side of the point indicated on the abscissa by $\alpha_1$. As seen, the voltage is generally constantly low on this side of $\alpha_1$ (which indicates the stoichiometrical air fuel ratio) the reason for which being until the stoichiometrical air fuel ratio is closely approached, there is an excess of oxygen remaining after all combustible material has been catalytically oxidized. Hence there is a partial pressure of oxygen prevailing on the surface of the measuring electrode until a mixture which is substantially stoichiometric is exposed to the measuring electrode. As the mixture becomes stoichiometric and exactly the amount of oxygen required to combust the hydrocarbon fuel is present therein, the oxidation of the remaining oxygen and hydrocarbon fuel will take place on the surface of the measuring electrode to reduce the concentration and thus the partial pressure of oxygen present thereon to approximately zero. Hence the voltage output of the sensor suddenly rises due to the sudden increase in the partial pressure difference between the two electrodes. However the partial pressure difference soon becomes constant as the air fuel mixture becomes richer and an excess of hydrocarbon fuel with respect to the oxygen present maintain the partial pressure of the oxygen on the surface of the measuring electrode effectively at zero. Thus, the steplike graph of FIG. 4A results.

In the case where a metal devoid of catalytic oxidizing properties is used to form the measuring electrode, the afore described oxidation reaction will not take place and the partial pressure (oxygen) on the surface of the measuring electrode will thus vary as the air fuel ratio varies. This is clearly shown graphically in FIG. 4B, wherein the output voltage of the sensor continuously increases as the air fuel mixture varies from lean to rich.

However as is also well known, the peak output voltages of both the afore mentioned sensors decrease with time (ie. age) and decrease of temperature. This effect is shown in both graphs in broken lines. It will be noted at this time that although the peak output voltage of the sensor having the measuring electrode made of the metal catalyst, changes with time and/or temperature, the point at which the sudden change in output voltage occurs does not change. However, in the case of the sensor equipped with the non oxidizing measuring electrode, a notable variation takes place. As seen in FIG. 4B, with the decrease in peak output voltage, the voltage $V_s$ which originally indicated a mixture having exactly a stoichiometric ratio (viz. $\alpha_1$), with the passing of time or variation of temperature, will be generated on exposure to a rich mixture having an air fuel ratio markedly lower (i.e. richer) than stoichiometric (viz. $\alpha_2$). This naturally leads to the situation wherein the closed loop control unit operatively connected thereto incorrectly controls the air fuel forming means. Hence the efficiency of air purifying and/or pollution controlling devices, especially so called "three way catalytic convertors," drops off undesirably.

In comparison the former type of sensor does not suffer from this drawback but lacks the ability to detect the transition of the air-fuel mixture from lean to rich or vice versa, until said transition very closely approaches the stoichiometric point. This, when coupled with the time lag inherent in the closed loop unit, permits the air fuel mixture to pass the stoichiometric point and become unwantedly rich or lean before control signals which rectify the transition are issued from the control unit. This results in a hunting of the air fuel mixture back and forth across the stoichiometric point.

Hence in an effort to overcome the drawbacks of the individual sensors i.e. the inability to rely on the output voltage of the second type to accurately indicate the correct air-fuel ratio and the inability of the first type to sense the transition of the air fuel mixture from lean to rich or vice versa unless very close to the stoichiometric point, it has been proposed to dispose both sensors in the exhaust system of a motor vehicle and connect them to a circuit which recalibrates the output voltage of the second type (i.e. the one which used the non catalytic measuring electrode) with respect to the point at which the marked voltage change occurs in the first type (i.e. the type using a measuring electrode made of a metal possessing catalytic oxidizing properties). This combination while solving the problems encountered by the individual sensors encounters the drawback that the use of two closely disposed or closely juxtaposed sensors proves to be bulky in arrangement and expensive; gas sensors being rather expensive components. Thus there still remains a need for a single sensor which posses the characteristics of the aforementioned combination of sensors.

SUMMARY OF THE INVENTION

In view of the foregoing a single sensor which is capable of replacing the bulky and expensive combination of sensors has been developed, the arrangement and construction of which confers upon it ruggedness and reliability while maintaining material and assembly costs within desirable limits.

In detail the sensor is characterized by a solid zirconia electrolyte having a generally cylindrical shape and formed with a stepped blind bore therein. The inner surface i.e. the surface defined by the blind bore has a platinum electrode suitably fixed thereto. This electrode functions as the atmospheric or reference electrode. The outer surface of the solid electrolyte has two separate and distinct electrodes formed thereon, the first made of platinum and the second gold. The atmospheric electrode is connected to a lead line through a tubular connector, the latter being firmly inserted into the aforementioned stepped blind bore. An insulating member having an annular configuration surrounds the portion of the tubular member not inserted into the blind bore. Two other lead wires pass through this insulator and are connected to the outer gold and platinum electrodes. Another small annular insulator is arranged about the cylindrical solid electrolyte to support same within the casing of the sensor. The aforementioned annular insulator also performs the same function.

In a second embodiment of the present invention the tubular connector is slightly modified and almost entirely inserted into the cylindrical body made of zirconia. A mixture of graphite and talcum powder is disposed between the inner atmospheric electrode and the outer surface of the tubular connector. This powder is packed in and retained by a locking ring slidingly disposed about the tubular connector and the inner electrode. This powder serves as an insulator to dampen shock and similar vibrations.

Thus it is an object of the present invention to provide a gas sensor which is suited to sensing the oxygen concentration in the exhaust gases flowing from an internal combustion engine which is compact and ruggedly constructed.

It is a further object of the present invention to provide a gas sensor which generates two distinct signals the first of which undergoes a marked and sudden change at or very near stoichiometric and the second a gradual or continuous change which corresponds to the variation of oxygen contained in the exhaust gases as the air fuel ratio approaches and/or passes the stoichiometric point.

It is yet another object of the present invention to provide a gas sensor which has one reference or atmospheric electrode and two measuring electrodes, the first made of a metal possessing catalytic properties and the other which is devoid of said catalytic properties.

Yet another object of the present invention is to provide a gas sensor which has a single body of solid electrolyte on which both of the aforementioned measuring electrodes are fixedly attached.

BRIEF DESCRIPTION OF THE DRAWINGS

Other features, advantages and objects of the present invention will become more clearly understood as the description proceeds taken in conjunction with the accompanying drawings in which.

Figure 1:
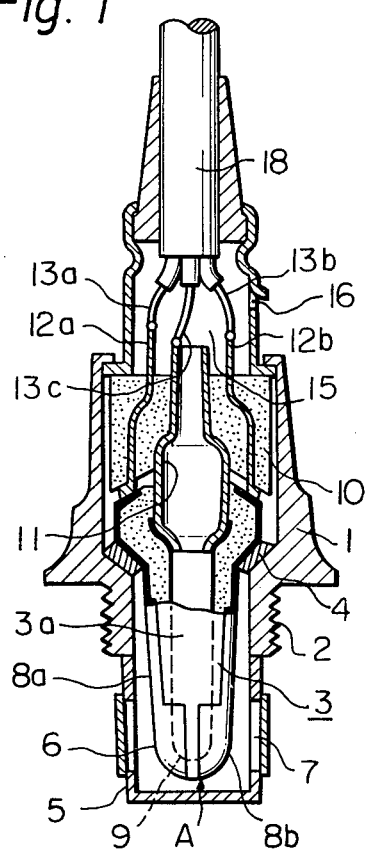
FIG. 1 is a partially sectioned view of a gas sensor according to first embodiment of the present invention.
Figure 2:
FIG. 2 is a view showing the end of the solid electrolyte and the two measuring electrodes which characterize the present invention.

Let us now look to FIG. 1 wherein the first preferred embodiment of the present invention is shown. The numeral 1 denotes the body or casing which defines therein the sensor proper. Formed on the casing 1 is a threaded portion 2 which serves to secure the sensor in the exhaust system of the motor vehicle in which it is to be operatively disposed. Disposed within the casing 1 is a generally tapered, cylindrical body of solid electrolyte 3 which is in this case preferably zirconia[$ZrO_2$]. The numeral 4 denotes an annular insulating member disposed between the solid electrolyte and the casing 1 to insulate the electrolyte from shock and undesired electrical contact with the casing and also to divide the casing hermetically into two chambers. A cover member 5 is fixedly attached to or formed integrally with the lower portion of the casing 1 and arranged thus to be exposed to the flow of the exhaust gases. Formed in the cover member 5 are a plurality of slits 7 which permit the entry of the exhaust gases into the chamber 6 which is defined within the casing 1 between the end thereof and the annular insulating member 4. Now as seen in the drawings, a platinum electrode 8a is fixedly secured to the left portion of the electrolyte 3 and a gold electrode 8b fixedly secured to the corresponding right portion of the electrolyte 3. If we briefly look at FIG. 2 the configuration of the two electrodes will become more clearly understood. As shown the two electrodes 8a and 8b have somewhat semi cylindrical shapes and are arranged on the electrolyte so as to be insulatingly separated by a sufficiently large gap. Once again referring to FIG. 1 it will be noted that another electrode 9 is fixedly attached to the surface of a blind bore (no numeral) formed within the body of solid electrolyte 3. The open end of the blind bore has a generally cylindrical connector 11 firmly inserted therein so as to form a good electrical contact between the electrode 9 formed on the surface of the bore. This electrode is preferably formed of platinum and will be referred to as the atmospheric electrode hereafter.

Disposed about the upper portion of the cylindrical connector 11 i.e. Substantially that portion which is not inserted in the aforementioned blind bore, is a supporting and insulating member 10. As seen two lead wires 12a and 12b pass through the aforementioned insulating member 10 and are fixed at their one ends to the platinum and gold electrodes 8a and 8b respectively. It will be noted that the cylindrical connector 11 is open at both ends so that the platinum atmospheric electrode 9 is exposed to atmospheric air permitted to enter the aforementioned blind bore via the cylindrical connector and a hole or air port 16 formed in the upper portion or cap of the casing 1. The cap portion of the casing through which the air port 16 is formed is arranged as shown to define an atmospheric chamber 15 and also press the supporting and insulating member 10 downwardly (as seen in the drawings) to urge the two lead wires 12a and 12b into firm contact with the surfaces of the two measuring electrodes 8a and 8b. To facilitate this the upper portion of the solid electrolyte is formed with a chamfer and the lower edge of the supporting and insulating member 10 is formed with a concavity which exactly matches the aforementioned chamfer. A main lead line 18 is arranged to appropriately enter the casing 1 through the topmost portion of the casing cap as shown. This main lead line contains therein three lead lines each of which are connected to one of the aforementioned electrodes. As can be seen the end of the lead line 13c is soldered or otherwise electrically connected to the top of the cylindrical connector 11, while the ends of the two lead wires 12a and 12b are connected at their respective end to the lead lines 13a and 13b. As will be appreciated by those skilled in the art, assembly of the sensor is facilated by this arrangement viz. It is possible to insert the lead wires through the supporting and insulating member 10 into the casing 1 so that the ends of the lead wires are firmly pressed against the two electrodes 8a and 8b; then solder weld otherwise join the lead lines and the lead wires and cylindrical connector together. Finally by pressing the cap portion of the casing into place very firm contact between the lead wires and the two electrodes 8a and 8b is established. Of course if desired the lead wires can be otherwise and additionally connected to the electrodes via a suitable bond or weld which does not unduly contaminate or poison the electrodes.

In operation the exhaust gases are permitted to enter the chamber 6 through the slits 7 to contact the surfaces of the two electrodes 8a and 8b. Simultaneously air is permitted to enter through the air port which is constantly open to contact the atmospheric electrode 9. The gases contacting the platinum electrode 8a undergo a catalytic oxidation reaction as previously described. However the gases contacting the gold electrode 8b do not undergo such a reaction thus the afore described two different signals are generated.

Figure 3:
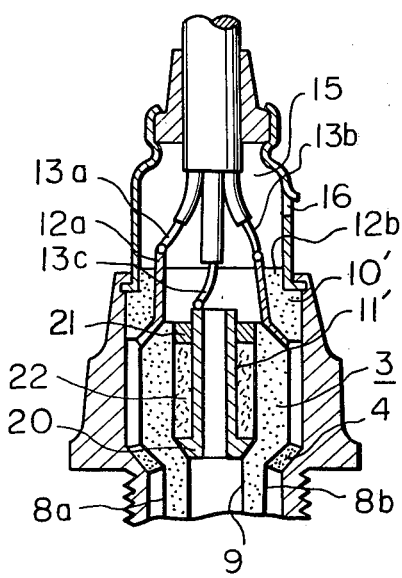
FIG. 3 is a partially sectioned view of a portion of a second preferred embodiment of present invention.
Figure 4A:
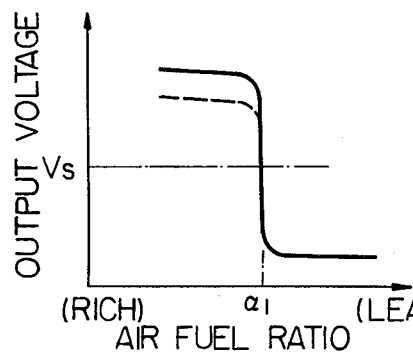
FIGS. 4A and 4B are graphs showing the relationship between the output voltage and the air fuel ratio of the exhaust gases for the two types of sensor which are included in the sensor of the invention.
Figure 4B:
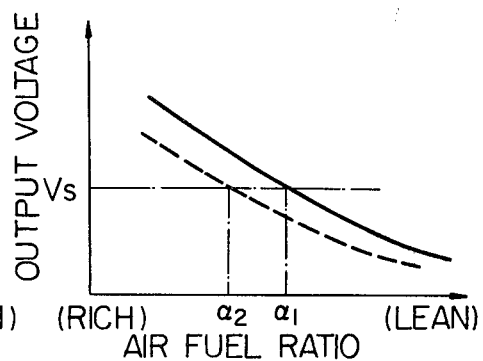

FIG. 3 shows a second preferred embodiment of the present invention. In this case the overall length of the sensor can be reduced via the construction which will be detailed hereafter. The numeral 11' indicates a cylindrical connector the function of which is identical with that of the first embodiment but the configuration of which permits it to be almost entirely inserted into the blind bore formed in the electrolyte body 3. As seen the lower portion 20 of the cylindrical connector 11' is formed with a chamber which matchingly engages a step formed in the bore. This arrangement limits the depth to which the connector can be inserted. The main elongate portion of the connector 11' is formed so as to have a diameter less than that portion 20 on which the chamfer is formed. Packed between this elongate portion and the platinum electrode 9 formed on the inner surface of the bore is a mixture of talcum and graphite powder. As shown a locking ring 21 as it will be referred to hereinafter is slidingly fitted on the elongate portion of the cylindrical connector 11' and so sized as to be press-fitable into the annular space defined between the connector 11' and the solid electrolyte body 3 and thus dust-tightly seal in the aforementioned powder mixture. The function of powder just described is to shock absorbingly support the cylindrical connector 11'. A supporting and insulating member 10' which is considerably smaller than that used in the previous embodiment is inserted into the upper portion of the casing 1. In this case the supporting and insulating member 10' is not disposed about the cylindrical connector and has the two lead wires 12a and 12b disposed along the surface thereof. As before, however, the supporting and insulating member 10' is arranged to firmly press the ends of the lead wires against the surfaces of the two electrodes 8a and 8b. This is facilitated by a step formed on the upper and outer shoulder of the supporting and insulating member 10' which is arranged to fittingly receive the flanged end of the cap portion so that when the cap is inserted into the casing 1 it is urged downwardly to press the ends of the lead wires against the chamfered upper end of the electrolyte body 3 and the electrodes 8a, 8b formed thereon.

It will be appreciated that, although reference has been made to the use of platinum and gold measuring electrodes, it is possible to use a poisoned platinum electrode in place of the gold electrode, the poisoned electrode of course exhibiting no catalysing properties and furthermore any other suitable metal catalyst in place of platinum and gold in both the reference and measuring electrodes if so desired.

What is claimed is:

1. In a single oxygen sensor unit for an internal combustion engine equipped with an electronic closed loop feed back control system for controlling the ratio of an air fuel mixture fed to the combustion chambers of said internal combustion engine, said sensor unit being directly disposable through the wall of an exhaust conduit of said internal combustion engine with one end thereof directly exposed to the flow of exhaust gases flowing therein and being provided with three electrical terminals, each of said terminals being electrically isolated from each other and said exhaust conduit and each being individually connected to said closed loop control system for supplying thereto two distinct signals, each of said signals being representative of a concentration of oxygen in the exhaust gases passing over the single oxygen sensor unit, one of said signals being used to recalibrate said closed loop feed back control system to compensate for a variation in the other signal with aging of said single oxygen sensor unit and with variation of the temperature thereof, said single oxygen sensor unit including:

an elongate cylindrical casing having a cap portion at a first end thereof, a thread portion formed in the exterior of said casing between said first end and a second end for securing said sensor in the exhaust conduit, said casing having a plurality of openings formed therein near said second end to permit the passage of said exhaust gases through and into said casing;

an elongate body of solid electrolyte which has a generally tapered cylindrical shape with a smoothly rounded nose portion, said body of solid electrolyte being formed with a blind stepped bore therein, said blind bore terminating near said nose portion, the surface of said blind bore defining a first surface and the outer surface of said body of solid electrolyte defining a second surface, said blind bore being oriented to direct the open end of said blind bore toward said first end of said casing and be fluidly communicated with the ambient atmosphere through holes formed in said cap portion;

a first electrode made of platinum formed in said first surface to act as a reference electrode;

a first annular support member disposed between said casing and said body of solid electrolyte so as to hermetically divide said casing into first and second chambers, said first chamber being located between said first annular support member and said first end of said casing and said second chamber being located between said first annular support member and said second end of said casing, said second chamber being fluidly communicated with said exhaust conduit through said plurality of openings;

a cylindrical connector, a portion of which is received in said blind bore to be in electrical contact with said first electrode; and a second annular support member disposed in said casing to receive a portion of said cylindrical connector in the circular opening formed therein;

the improvement comprising:

two lead lines passing through said second annular support member and being pressed against said second surface by pressure applied thereto by said cap portion, the ends of said two lead wires and said cylindrical connector which extends toward said first end of said casing defining said three terminals;

a second electrode made of platinum formed on said second surface in a manner to be in electrical contact with one of said two lead lines, to cover a portion of said second surface and extend longitudinally along said second surface from said nose portion in the direction of said first end of said casing;

a third electrode made of a metal selected from the group of gold and platinum poisoned with a suitable poison so as to be devoid of catalytic properties, said third electrode being formed on said second surface in a manner to be in electrical contact with the other of said two lead lines, cover a portion of said second surface, extend along said second surface from said nose portion in the direction of said first end of said casing and be electrically isolated from said second electrode;

said second and third electrodes in said second chamber being diametrically oppositely positioned relative to each other on said second surface such that exhaust gases entering said second chamber are caused to simultaneously contact the closely juxtaposed second and third electrodes.

2. The oxygen sensor as claimed in claim 1 wherein said cylindrical connector further comprises a portion having a diameter less than the internal diameter of the portion of said stepped bore in which said cylindrical connector is received to define an annular space;

a powder packed into said annular space to absorb shock applied to said single oxygen sensor unit; and a locking ring snugly received in said blind bore and on said cylindrical connector to close said annular space to retain said powder therein.

* * * * *